United States Patent [19]

Capone

[11] Patent Number: 4,784,728
[45] Date of Patent: Nov. 15, 1988

[54] OXYGEN MEASURING APPARATUS AND METHOD WITH AUTOMATIC TEMPERATURE COMPENSATION

[75] Inventor: David M. Capone, Oakmont, Pa.

[73] Assignee: Ametek, Inc., New York, N.Y.

[21] Appl. No.: 65,581

[22] Filed: Jun. 23, 1987

[51] Int. Cl.$^4$ ............................................. G01N 27/58
[52] U.S. Cl. ................................... 204/1 T; 204/408; 204/427; 204/428
[58] Field of Search ............... 204/408, 427, 428, 429, 204/406, 15

[56] References Cited

U.S. PATENT DOCUMENTS

| | | | |
|---|---|---|---|
| 3,347,767 | 10/1967 | Hickam | 204/195 |
| 3,859,192 | 1/1975 | Barnes et al. | 204/195 |
| 3,865,707 | 2/1975 | Sayles | 204/427 X |
| 4,284,487 | 8/1981 | Barnes et al. | 204/195 |
| 4,659,435 | 4/1987 | Brothers et al. | 204/1 T |

FOREIGN PATENT DOCUMENTS 29200 12/1968 Japan ......................................... 204/408

Primary Examiner—G. L. Kaplan
Attorney, Agent, or Firm—Webb, Burden, Ziesenheim & Webb

[57] ABSTRACT

During the measurement of oxygen content of a gas with a solid electrolyte material capable of oxygen ion conductivity the electrolyte is heated to maintain a constant control temperature. If the ambient temperature changes, an offset or error is introduced into the oxygen measurement. An apparatus and method is provided to automatically compensate for any such offset. Thermocouple means are provided in series with the electrolyte circuit so that a thermal emf if generated due to any differential between ambient and control temperatures. The thermocouples are arranged to generate a net thermal emf which opposes the emf generated by the electrolyte by an amount which automatically compensates for any offset due to the temperature differential. If the ambient and control temperatures are the same, there will be no offset and no net thermal emf.

18 Claims, 1 Drawing Sheet

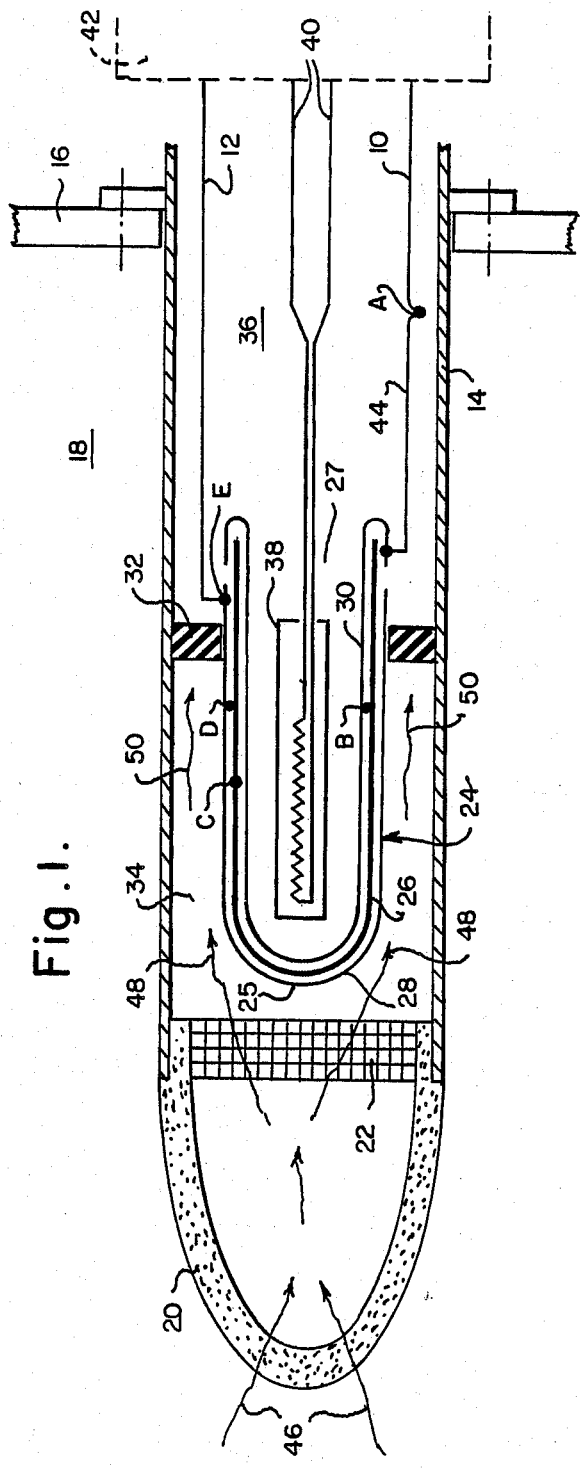
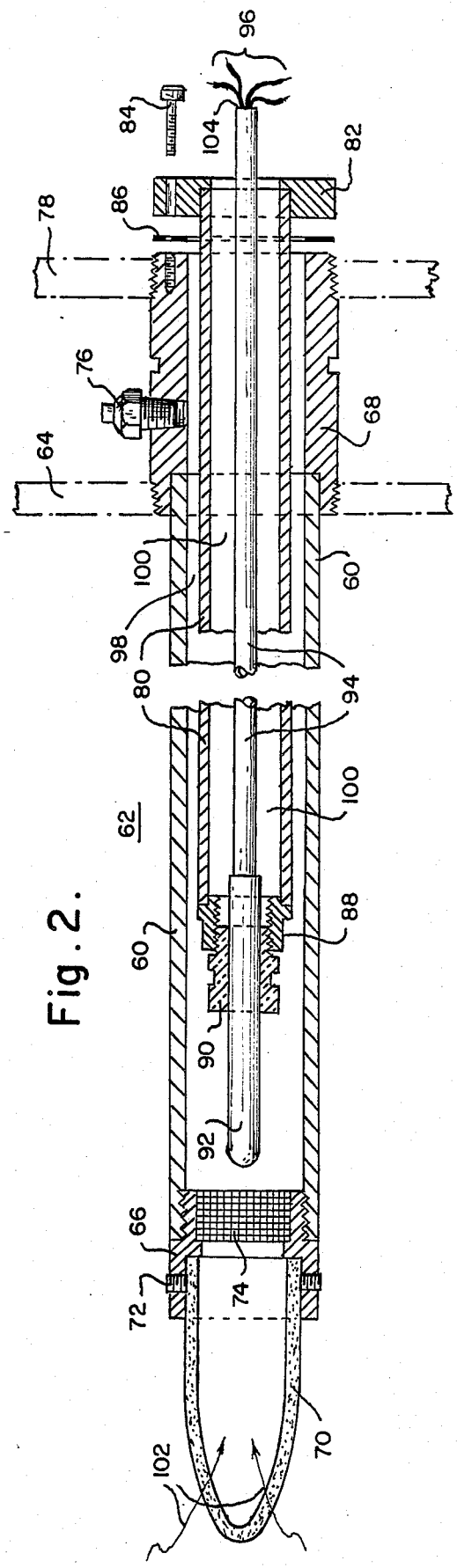
Fig. 1.
Fig. 2.

OXYGEN MEASURING APPARATUS AND METHOD WITH AUTOMATIC TEMPERATURE COMPENSATION

This invention relates to an apparatus and method for measuring the oxygen content of a gas.

More particularly, this invention relates to an apparatus and method for measuring the oxygen content of a gas employing a solid electrolyte material capable of oxygen ion conductivity, such as a stabilized zirconia solid electrolyte cell. Although the present invention can be used to measure the oxygen content of the gas in any flowing stream, the invention is described herein particularly for the measurement of the oxygen content of flue gas in a combustion process such as a boiler.

In the measurement of the oxygen content of a flue gas employing a solid electrolytic cell, a heater is disposed in close proximity to or within the cell to maintain a constant control temperature at the cell. Accuracy of measurement requires the control temperature at the cell be the same as the temperature of the flue gas stream under measurement, which is referred to as the ambient temperature. The measuring instrument is calibrated to indicate oxygen content, concentration or partial pressure in the gas under measurement assuming a constant ambient temperature. If the ambient temperature deviates from the set control temperature at the electrolytic cell, an offset or error is introduced into the indicated measurement of oxygen concentration. The apparatus and method of this invention automatically compensates for any deviation in ambient temperature from the control temperature.

The electrochemical cell produces an electrical potential or electromotive force (emf) which is indicative of the oxygen content in the flue gas. If the control temperature established by the heater within the cell and the ambient temperature outside the cell are the same, there will be no cell offset due to temperature. If the temperature within the cell and the ambient temperature are different, there will be a cell offset due to temperature, i.e. an error or deviation from the correct cell indication of oxygen content in the flue gas. The offet arises due to electrical noise generated at the various junctions of dissimilar metals in the series circuit of which the sensor cell is a part. The various junctions of dissimilar metals produce electrical thermocouple effects which introduce undesired emf's into the circuit.

In a preferable mode, this invention utilizes a thermocouple system in the series circuit which automatically compensates for any differences between the cell temperature and the ambient temperature and which automatically compensates for cell offset due to temperature. The thermocouple system of this invention comprises a series circuit including thermocouple pairs which are arranged in the circuit to prevent any emf effect due to temperature variation from reaching the oxygen indicating instrument. In the circuit the thermocouples in each pair comprise similar but oppositely connected metals, whereby the thermocouples in each pair produce opposing emf's, whereby no net emf from the pair is produced when the cell temperature and the ambient temperature are the same. When there is a differential between the cell temperature and the ambient temperature, the opposing thermocouples in the pairs of thermocouples produce a net thermal emf. The net thermal emf opposes the emf generated at the cell due to oxygen concentration by an amount equal to the cell offset and thereby compensates for any cell offset due to temperature.

If there is no differential between the cell temperature as etablished by the cell heater and the ambient temperature as established by the flue gases, then the temperatures on the inside of the cell and on the ouside of the cell will be the same. In this case, the similar but opposite thermocouples in the series will each generate emf's, but the emf's generated by each thermocouple of a pair will be equal and opposite and thereby cancel each other. There is no cell offset due to temperature when the cell temperature and the ambient temperature are the same so that no net emf generated by the series of thermocouples is required.

On the other hand, if there is a differential between the cell temperature as established by the cell heater and the ambient temperature as established by the flue gases, then the temperatures on the inside of the cell and on the outside of the cell will be different. In this case, the similar but opposite thermocouples in the series will each generate an emf but these emf's will be unequal as well as opposite so that there will be a net emf generated by the thermocouple pairs. There is a cell offset due to temperature when the cell temperature and the ambient temperature are different, and in the present system the net emf generated by the series of thermocouples will oppose and thereby compensate for the cell offset to an extent which prevents any emf effect due to temperature variation from reaching the measuring instrument.

In accordance with this invention, automatic compensation for cell offset due to a difference between oxygen cell temperature and ambient temperature can be achieved in other ways. For example, temperature measuring means can be installed to measure the ambient temperature of the boiler flue gases and the ambient temperature signal can be supplied to a microcomputer which is programmed to correct the oxygen measuring instrument for any offset due to deviation of ambient temperature from the temperature of the cell.

The apparatus of this invention can comprise a tube of solid electrolyte material capable of oxygen ion conductivity, said tube having a closed end in communication with the gas under measurement and an open end exposed to atmospheric air. A first electrode is disposed on the outside surface of the tube and a second electrode is disposed on the inside surface of the tube. A heater is disposed in close proximity to or within the tube for eeating the tube and maintaining a constant control temperature at the tube. Oxygen indicating means is provided remote from the tube. First wire means extends between the first electrode and the indicating means and second wire means extends between the second electrode and the indicating means. Temperature measuring means is also connected to the indicating means for measuring the ambient temperature around said tube. The apparatus includes temperature compensating means for automatically compensating for any offset in the indication of oxygen content due to a difference between the ambient temperature and the control temperature.

As indicated above, the temperature compensation means can comprise a microcomputer disposed at the indicating instrument. Preferably, the temperature compensating means comprises thermocouple junctions in series with the electrolytic cell. The thermocouple junctions measure the differential between the ambient and control temperatures and generate a net thermal emf which opposes the electrolytic cell emf due to oxygen conductivity by an amount equal to any cell offset due to temperature, thereby automatically compensating for any offset arising due to a difference between ambient and control temperatures.

In a more particular description of the thermocouple mode of this invention, the tube of solid electrolyte has a closed end and an open end, the closed end is in communication with the flue gas and the open end is in communication with atmospheric air. A first electrode is disposed on the inside surface of said tube. A second electrode is disposed on the outside surface of the tube. A heater is disposed within the tube for heating said tube. Oxygen indicating means is provided for indicating the oxygen content of the flue gas. First and second wire means in series extend between said first electrode and the oxygen indicating means. The first and second wire means comprise dissimilar metals, respectively, and are joined to each other to form a first thermocouple junction at a position removed from said first electrode in an ambient temperature zone. The first wire means comprises the same metal as said first electrode and is connected to said first electrode. The second wire means is connected to the oxygen indicating means. Third wire means extends between the second electrode and the oxygen indicating means. The third wire means and the second electrode comprise dissimilar metals, respectively, and are joined to each other to form a second thermocouple junction. The third wire means comprises the same metal as the second wire means. The first and second thermocouple junctions generate first and second thermal emf's respectively if the first thermocouple junction, which is at ambient temperature, and the second thermocouple junction, which is at or near the cell temperature, are at different temperatures. This will occur if the ambient temperature and the cell temperature are different. The first and second thermal emf's oppose each other to provide a net thermal emf. The net thermal emf opposes the emf generated by the cell in response to oxygen conductivity to automatically compensate for any offset in cell measurement due to a differential between the ambient and control temperatures. If the ambient and control emf's are the same, there will be no net thermal emf and no offset.

This invention also relates to an advantageous probe apparatus for supporting the electrolytic cell within a boiler or other vessel containing an oxygen containing gas. The probe comprises an outer cylindrical housing having one end for extending into a stream of said gas and another end for mounting at the wall of a vessel containing said gas. An inner cylindrical housing is disposed inside of said outer cylindrical housing to provide an annular space between said inner and outer cylindrical housings. A tube of solid electrolyte material capable of oxygen ion conductivity having a closed end and an open end is supported within said inner cylindrical housing with the open end facing the interior of said inner housing and the closed end projecting outwardly towards said one end of said outer housing. Sealing means is provided between the tube and the inner cylindrical housing to seal the interior of the inner housing from the interior of the outer housing. Closure means is provided at said another end of the apparatus for closing said annular space from the atmosphere. Calibration port and plug means open to said annular space is provided for periodically supplying a calibration oxygen-containing gas to said annular space.

In terms of process, this invention relates to a method for measuring the oxygen content of a gas comprising passing said gas to the outside of a tube of solid electrolyte material capable of oxygen ion conductivity, said tube having a closed end in communication with said gas and an open end, and said tube having an outside electrode and an inside electrode. The open end of the tube is exposed to atmospheric air. The tube is heated to maintain a control temperature. The oxygen ion conductivity generates a cell emf and this emf signal is passed to an oxygen indicating instrument for indicating the oxygen content of the gas. The ambient temperature in the vicinity of said tube is measured with temperature measuring means to produce a thermal emf signal which is passed to the oxygen indicating instrument. Based on the thermal emf signal, the oxygen indicating means automatically compensates for an offset, if any, in oxygen content indication due to a difference between said ambient temperature and said control temperature.

Electrochemical cells for analyzing for oxygen content in a gas stream by measuring oxygen partial pressure are well known and suitable cells for this purpose are disclosed in U.S. Pat. Nos. 3,597,345, 3,865,707 and 3,869,370, which are hereby incorporated by reference.

This invention will be more fully understood by reference to the accompanying drawings in which FIG. 1 shows the sensor cell and thermocouple circuit of this invention, and FIG. 2 shows an advantageous probe body design for containing the sensor cell and thermocouple circuit.

The sensor series circuit of this invention is illustrated in FIG. 1. FIG. 1 shows five emf generators in the sensor series circuit. These five emf generators are shown by letter designation in FIG. 1 and are listed in the following table.

| Position | Type of emf generator | Emf type |
|---|---|---|
| A | Ni—Pt thermocouple | Thermal |
| B | Pt—$ZrO_2$ thermocouple | Thermal |
| C | Electrochemical cell | Electrochemical |
| D | $ZrO_2$—Pt thermocouple | Thermal |
| E | Pt—Ni thermocouple | Thermal |

Referring to the above table, it is seen that the thermocouples in pair A and E are similar but opposite and the thermocouples in pair B and D are similar but opposite. Therefore, if the temperatures at positions A, B, C, D and E are all the same the thermal emf's generated by similar but opposite thermocouples A and E will be equal and opposite and will cancel each other and the thermal emf's generated by similar but opposite thermocouples B and D will be equal and opposite and will cancel each other. Thereby, if the temperatures at each of the positions are the same the net emf generated by the series circuit will be the cell emf with no offset due to temperature.

If some or all of the temperatures at positions A, B, C, D and E are different from each other, there will be unequal thermal emf's generated by the similar but opposite thermocouples. The thermal emf's generated by similar but opposite thermocouples A and E will be unequal and opposite, resulting in a first net thermal emf. Also, the thermal emf's generated by similar but opposite thermocouples B and D will be unequal and opposite, resulting in a second net thermal emf. Thereby, if the temperatures at each of the positions are different there will be one or more net thermal emf's generated. The sum of these net thermal emf's will be equal to the cell offset due to temperature effects. The thermocouples are arranged in the series circuit so that the sum of the net thermal emf's will be not only equal to but also opposite to the cell offset emf, and will thereby cancel the cell offset emf. Thereby, the thermocouple arrangement in the electrical series circuit automatically cancels any cell offset due to thermal effects.

Referring again to FIG. 1, probe body or housing 14 is inserted through a hole in boiler wall 16 and is fixedly mounted on wall 16 by any suitable means so that it protrudes into boiler interior 18. The forward end of housing 14 is enclosed by filter 20 and flame arrestor 22. Filter 20 removes solid particulates from the flue gas and can comprise carborundum ceramic. Flame arrestor 22 can comprise knitted stainless steel. Filter 20 and flame arrestor 22 are optional equipment. Electrochemical cell 24 is supported within cylindrical housing 14 and is capable of conducting oxygen ions to provide an electrochemical emf signal indicative of the oxygen content of a gas. The materials comprising cell 24 are well known. They include solid electrolyte material capable of oxygen ion conductivity. Cell 24 can comprise solid solutions of oxides of a tetravalent element from the group consisting of zirconium, thorium and hafnium and an oxide of a metal such as calcuim, barium, strontium and lanthanum. A common composition comprises a solid solution of zirconium oxide and yttrium oxide, commonly referred to as stabilized zirconia ($ZrO_2$).

Cell 24 can comprise stabilized zirconia electrolyte 26 coated with outer platinum electrode 28 and a separate inner platinum electrode 30. Cell 24 is ubular and comprises a closed end 25 and an open end 27. Closed end 25 comprises the outside of the cell and open end 27 provides access to the inside of the cell. The platinum electrodes are gas permeable. Cell 24 is mounted on seal 32 which separates flue gas circulating zone 34 from atmospheric air-containing zone 36. Thereby, the outside of the cell is exposed to flue gases and the inside is exposed to atmospheric air. Heater unit 38 having electrical power leads 40 is disposed within electrochemical cell 24 and maintains a constant control temperature within the cell which can be equal to the normal ambient temperature in zone 18.

The series circuit including zirconia electrolyte C extends from nickel wire 10 to nickel wire 12. Wires comprising alloys having thermoelectric properties similar to nickel, such as constantan, can be substituted for nickel wires herein. Wires 10 and 12 can terminate at remote oxygen concentration indicating instrument 42. Nickel wire 10 forms thermocouple junction A with platinum wire 44. Thermocouple junction A is located outside of and away from cell 24 so that it is under the ambient temperature influence of boiler interior 18. Platinum wire 44 and inside platinum electrode 30 form a continuous conductor. Wires comprising alloys having thermoelectric properties similar to platinum, such as chromel, can be substituted for platinum wires herein. Platinum electrode 30 forms a continuous junction with zirconia electrolyte C, as indicated schematically at B. The circuit then passes through electrolyte C. In turn, platinum electrode 28 forms a continuous junction with zirconia electrolyte C, as indicated schematically at D. Finally, outside platinum electrode 28 forms junction E with nickel wire 12 to complete the circuit.

Flue gases flowing in boiler chamber 18 pass through filter 20 as indicated at 46 and then pass through flame arrestor 22 as indicated at 48 to enter chamber 34. Filter 20 and flame arrestor 22 are both optional equipment. The flue gases can traverse chamber 34 as indicated at 50 but can proceed only as far as seal 32, which serves as a barrier against further flow of the flue gases. Chamber 36 is therefore protected against inflow of flue gases but is exposed to and contains atmospheric air. Thereby, outside porous electrode 28 of cell 24 is exposed to flue gases and inside porous electrode 30 of cell 24 is exposed to atmospheric air.

FIG. 1 illustrates the five emf-generating elements of the series circuit. First, an emf-generating thermocouple at nickel-platinum junction A which is under the influence of the ambient temperature in boiler 18. Secondly, an emf-generating thermocouple at platinum-zirconia junction B, which is under the influence of the outer skin temperature of cell 24. Third, the electrochemical emf generated by zirconia electrolyte C, which is determined by the oxygen concentration of flue gas 46. Fourth, an emf-generating thermocouple at zirconia-platinum junction D, which is under the influenceof heater 28. Fifth, an emf-generating thermocouple at platinum-nickel junction E which is under the influence of basically the outer skin temperature of cell 24.

It is seen that the four thermocouples A, B, D and E comprise two pairs of similar but opposite thermocouples. Thermocouple A is a Ni-Pt thermocouple while thermocouple E is a Pt-Ni thermocouple. Therefore, thermocouples A and E produce opposing emf's. Thermocouple B is a platinum-zirconia thermocouple while thermocouple D is a zirconia-platinum thermocouple. Therefore, thermocouples B and D produce opposing emf's. If all the thermocouples are at the same temperature, they produce no net thermocouple emf and the only emf produced by the series circuit is the electrochemical emf produced by the zirconia cell. If the thermocouples are not at the same temperature, there is a net thermocouple emf which automatically cancels any thermal offset in the electrochemical generated emf.

FIG. 2 shows an advantageous housing arrangement for electrolytic cell 24 which provides ease of servicing and calibrating. Because the housing arrangement of FIG. 1 utilizes seal 32 extending between cell 24 and housing 14 to secure the cell to the housing, the entire housing must be removed whenever it is desired to remove cell 24 for servicing. Furthermore, seal 32 prevents a calibration gas from reaching the exterior surface of cell 24 for calibration purposes. The embodiment of FIG. 2 avoids these difficulties by utilizing a seal arrangement which provides an uninterrupted annular space between the cell and the outer housing so that calibration gas can reach the exterior of the cell and so that the cell can be easily removed from the housing for servicing.

Referring to FIG. 2, exterior cylindrical housing 60 extends into boiler space 62 through mounting flange 64 which can be attached to a boiler wall at an opening, not shown. Housing 60 has an extension on the end extending furthest into boiler space 62 comprising coupling 66 and housing 60 has an extension into the atmosphere comprising coupling 68. Coupling 66 supports filter 70 by means of lock screws 72 and also supports flame arrestor 74. Coupling 68 is provided with a calibration port closed by plug 76 and supports electrical terminal case 78.

Internal cylindrical housing 80 is secured to flange 82 on one end. Flange 82 is mounted onto coupling 68 by means of bolts 84 and sealing gasket 86 provided between flange 82 and coupling 68. The opposite end of internal housing 80 is provided with collar 88 which supports cell seal 90 which in turn supports electrolytic cell 92. Conduit 94 extends from cell 92 for carrying thermocouple and heater electrical wires 96 from cell 92 to terminal case 78.

The embodiment of FIG. 2 provides continuous and uninterrupted annular space 98 between exterior housing 60 and interior housing 80. It also provides continuous and uninterrupted annular space 100 between interior housing 80 and conduit 94. Flue gases indicated at 102 flow inwardly through filter 70 and through flame arrestor 74 to the exterior of cell 92. The flue gases have access to annulus 98 but are prevented from escape to the atmosphere by means of flange 82 and gasket 86. The atmosphere has access to the interior of cell 92 through end opening 104 in conduit 94.

An advantage of the structure of FIG. 2 is that electrolytic cell 92 can be easily removed for servicing merely by unscrewing bolts 84 and moving flange 82 horizontally outwardly, as shown. Inner housing 80 and cell 92 are integral with flange 82 and are removed therewith. Another advantage of the structure of FIG. 2 is that cell 92 can be calibrated in place when the boiler is not operating. Calibration occurs by removing plug 76 and introducing a gas of known oxygen concentration into the calibration gas port. The calibration gas travels along annular space 98 to the exterior of cell 92.

I claim:

1. An apparatus for measuring the oxygen content of a gas comprising;
    a tube of solid electrolyte material capable of oxygen ion conductivity, said tube having a closed end in communication with said gas and an open end in communication with atmospheric air, a first electrode disposed on the inside surface of said tube, a second electrode disposed on the outside surface of said tube;
    heater means disposed in close proximity to said tube for heating said tube for maintaining a control temperature at said tube;
    oxygen indicating means for indicating the oxygen content of said gas;
    first wire means extending between said first electrode and said indicating means;
    second wire means extending between said second electrode and said indicating means;
    temperature measuring means connected to said indicating means for measuring the ambient temperature around said tube; and
    ambient temperature compensating means in said apparatus for automatically compensating for any offset in said measurement of oxygen content based on a difference between said ambient temperature and said control temperature.

2. The apparatus of claim 1 wherein said heater means is disposed within said tube.

3. The apparatus of claim 1 wherein said first electrode and said second electrode are platinum electrodes.

4. The apparatus of claim 1 wherein said tube comprises stabilized zirconia.

5. The apparatus of claim 1 wherein said first wire means and said second wire means comprise a material selected from the group consisting of nickel and constantan.

6. The apparatus of claim 1 wherein said ambient temperature compensating means is in said oxygen indicating means.

7. The apparatus of claim 1 wherein said ambient temperature compensating means includes temperature measuring means.

8. The apparatus of claim 1 wherein said ambient temperature compensating means includes a thermocouple junction in said first wire means.

9. An apparatus for measuring the oxygen content of a gas comprising;
    a tube of solid electrolyte material capable of oxygen ion conductivity, said tube having a closed end in communication with said gas and an open end in communication with atmospheric air, a first electrode disposed on the inside surface of said tube, a second electrode disposed on the outside surface of said tube;
    a heater in close proximity to said tube for heating said tube;
    indicating means for indicating the oxygen content of said gas;
    first and second electrical wire means in series extending between said first electrode and said indicating means;
    said first and second wire means comprising dissimilar metals, respectively, and joined to each other at a position removed from said first electrode to form a first thermocouple junction;
    said first wire means comprising the same metal as said first electrode and connected to said first electrode;
    said second wire means connected to said indicating means;
    third wire means extending between said second electrode and said indicating means;
    said third wire means and said second electrode comprising dissimilar metals, respectively, and joined to each other to form a second thermocouple junction;
    said third wire means comprising the same metal as said second wire means;
    said first and said second thermocouple junctions generating first and second emf's respectively; and
    said first and second emf's opposing each other.

10. The apparatus of claim 9 wherein said first electrode and said second electrode comprise platinum.

11. The apparatus of claim 9 wherein said first wire means comprises a material selected from the group consisting of platinum and chromel.

12. The apparatus of claim 9 wherein said second and said third wire means each comprise a material selected from the group consisting of nickel and constantan.

13. An apparatus for measuring the oxygen content of a gas comprising;
    a tube of solid electrolyte material capable of oxygen ion conductivity, said tube having a closed end in communication with said gas and an open end in communication with atmospheric air, a first platinum electrode disposed on the inside surface of said tube, a second platinum electrode disposed on the outside surface of said tube;
    a heater disposed within said tube for heating said tube;
    indicating means for indicating the oxygen content of said gas;

first and second electrical wire means in series extending between said first electrode and said measuring means;

said first and second wire means comprising dissimilar metals, respectively, and joined to each other at a position removed from said first electrode to form a first thermocouple junction;

said first wire means comprising platinum and connected to said first electrode;

said second wire means comprising nickel and connected to said indicating means;

third wire means extending between said second electrode and said indicating means; and said third wire means comprising nickel and joined to said second electrode to form a second thermocouple junction.

14. The apparatus of claim 13 wherein said gas is flue gas.

15. The apparatus of claim 13 wherein said electrolyte is stabilized zirconia.

16. A method for measuring the oxygen content of a gas comprising;

passing said gas to the outside of a tube of solid electrolyte material capable of oxygen ion conductivity, said tube having a closed end in communication with said gas and an open end in communication with atmospheric air, said tube having an outside electrode and an inside electrode;

heating said tube to maintain a control temperature at said tube;

the oxygen in said gas generating an electrical signal at said tube and passing said signal through said electrodes to an oxygen indicating means for indicating the oxygen content of said gas;

measuring the ambient temperature in the vicinity of said tube; and automatically compensating for any offset in indication of oxygen content due to a difference between said ambient temperature and said control temperature.

17. The method of claim 16 wherein said measurement of ambient temperature is a thermocouple measurement.

18. The method for measuring the oxygen content of a gas comprising;

passing said gas to the outside of a tube of solid electrolyte material capable of oxygen ion conductivity, said tube having a closed end in communication with said gas and an open end in communication with atmospheric air; said tube having an outside electrode and an inside electrode;

heating said tube to maintain a control temperature at said tube;

the oxygen in said gas generating a first electrical signal at said tube and passing said first electrical signal through said electrodes to an oxygen indicating means for indicating the oxygen content of said gas;

measuring by thermocouple the ambient temperature in the vicinity of said tube to produce a second electrical signal based on the difference between said control temperature and said ambient temperature;

passing said second electrical signal through said electrodes to said oxygen indicating means; and said first electrical signal and said second electrical signal opposing each other thereby automatically compensating for any offset in the indication of oxygen content due to a difference between said control temperature and said ambient temperature.

* * * * *